United States Patent
Agrawal et al.

(10) Patent No.: US 9,850,186 B2
(45) Date of Patent: Dec. 26, 2017

(54) PARAXYLENE SEPARATION PROCESS

(71) Applicant: ExxonMobil Chemical Patents Inc., Baytown, TX (US)

(72) Inventors: Gaurav Agrawal, Houston, TX (US); Michael W. Weber, Houston, TX (US); Michael Salciccioli, Houston, TX (US); John R. Porter, Lake City, MI (US); Dana L. Pilliod, League City, TX (US); Timothy P. Bender, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/375,754

(22) Filed: Dec. 12, 2016

(65) Prior Publication Data

US 2017/0247301 A1 Aug. 31, 2017

Related U.S. Application Data

(60) Provisional application No. 62/300,353, filed on Feb. 26, 2016.

(51) Int. Cl.
*C07C 5/27* (2006.01)

(52) U.S. Cl.
CPC .......... *C07C 5/2767* (2013.01); *C07C 5/2729* (2013.01)

(58) Field of Classification Search
None
See application file for complete search history.

(56) References Cited

U.S. PATENT DOCUMENTS

| | | | |
|---|---|---|---|
| 7,915,471 B2 | 3/2011 | Leflaive et al. | |
| 2011/0245573 A1* | 10/2011 | Porter | B01D 15/1835 585/830 |
| 2012/0302812 A1* | 11/2012 | Corradi | B01D 15/1835 585/821 |
| 2013/0158331 A1* | 6/2013 | Corradi | B01D 15/1828 585/820 |
| 2015/0246860 A1* | 9/2015 | Bender | C07C 6/123 585/303 |

(Continued)

OTHER PUBLICATIONS

Minceva, M. et al., "*Modeling and Simulation of a Simulated Moving Bed for the Separation of p-Xylene*," Industrial and Engineering Chemistry Research, 2002, 41, pp. 3454-3461.

*Primary Examiner* — Tam M Nguyen (57) ABSTRACT

A process for producing paraxylene is provided. The process includes separating a first mixture of $C_8$ aromatic hydrocarbons in a simulated moving bed apparatus using a desorbent to produce (i) an extract comprising ≥50.0 wt % of the paraxylene in the first mixture; (ii) a desorbent-rich raffinate comprising ≥75 wt % of the desorbent withdrawn, and (iii) an desorbent-lean raffinate comprising ≤25 wt % of the desorbent withdrawn in the desorbent-rich and desorbent-lean raffinates. The desorbent-lean raffinate can then, without an intervening separation step, be passed to a refinery process or a vapor phase isomerization reaction to produce an effluent comprising paraxylene in a greater concentration than the desorbent-lean raffinate. The desorbent-rich raffinate can be passed to a liquid phase isomerization reaction to produce an effluent comprising paraxylene in a greater concentration than the desorbent-rich raffinate.

25 Claims, 3 Drawing Sheets

(56) References Cited

U.S. PATENT DOCUMENTS

| | | |
|---|---|---|
| 2015/0266794 A1 | 9/2015 | Ou et al. |
| 2015/0307418 A1* | 10/2015 | Frey .................... C07C 1/20 585/321 |
| 2015/0376088 A1* | 12/2015 | Molinier .............. B01J 19/2445 585/314 |
| 2016/0145174 A1* | 5/2016 | Porter ................ B01D 15/1807 585/828 |
| 2016/0347689 A1* | 12/2016 | Whitchurch .............. C07C 7/04 |

* cited by examiner

PARAXYLENE SEPARATION PROCESS

PRIORITY

This application claims priority to and the benefit of U.S. Provisional Application No. 62/300,353, filed Feb. 26, 2016, the disclosure of which is incorporated herein by reference in its entirety.

FIELD OF THE INVENTION

The invention relates to a process for separating paraxylene from a multicomponent fluid mixture of $C_8$ aromatics, and more particularly to a process for separating paraxylene from such a fluid mixture by means of a simulated moving bed adsorption apparatus.

BACKGROUND OF THE INVENTION

Aromatic hydrocarbons, such as benzene, toluene, xylene, etc., are useful as fuels, solvents, and as feeds for various chemical processes. Of the xylenes, paraxylene is particularly useful for manufacturing phthalic acids such as terephthalic acid, which is an intermediate in the manufacture of synthetic fibers such as polyester fibers. Xylenes can be produced from naphtha, e.g., by catalytic reforming, with the reformate product containing a mixture of xylene isomers and ethylbenzene. Separating paraxylene from the mixture generally requires stringent separations, e.g., separations utilizing superfractionation and multistage refrigeration steps. Such separations are characterized by complexity, high energy-usage, and high cost.

Chromatographic separation is an alternative to more stringent separations, such as superfractionation, for removing paraxylene from a mixture of aromatic $C_8$ isomers. Chromatographic separation involves simulating a moving bed of selective adsorbent. Examples of commercial processes in which paraxylene is separated from aromatic $C_8$ isomers by simulated moving bed separation ("SMB") include PAREX, available from UOP, ELUXYL, available from Axens, and AROMAX, available from Toray.

Traditionally, there are two outlet streams in an SMB operation, raffinate and extract, for the recovery of the products. The raffinate stream may be isomerized and recycled to the paraxylene separation step to produce more paraxylene (commonly referred to as a xylene loop). Historically, xylene isomerization has been accomplished in the vapor phase. However, liquid isomerization units have recently found increasing use in paraxylene separation systems. One drawback of liquid phase isomerization is that liquid phase isomerization converts little or none of the ethylbenzene in the paraxylene-depleted stream, and as a result, the amount of ethylbenzene in the xylenes loop can build up to very high levels.

US 2015/0266794A discloses a xylene loop in which a paraxylene-containing extract and an ethylbenzene-containing raffinate are separated from a first mixture in a first separation stage to form a paraxylene-depleted raffinate. The paraxylene-depleted raffinate and the ethylbenzene-containing raffinate are withdrawn in such a way that the majority of the ethylbenzene (EB) is withdrawn in the ethylbenzene-containing raffinate. This uneven split in EB enables the process to primarily use liquid phase isomerization (LPI) for the paraxylene-depleted raffinate. The ethylbenzene-containing portion can be removed from the process to recover ethylbenzene or can be subjected to a vapor phase isomerization.

However, prior to isomerization, it generally is required to remove desorbent from the $C_8$ aromatics as the desorbent may crack during the isomerization, which can result into a downgrading of the desorbent, and is not economical. Typically, a SMB system using PDEB (para-diethylbenzene) as a desorbent ("heavy" SMB unit) will have an extract tower to separate desorbent from the extract stream which comprises paraxylene and desorbent, finishing tower(s) to remove any other lighter hydrocarbons, such as toluene remaining from the feed, from the paraxylene, and raffinate tower(s) to separate desorbent from the raffinate stream which comprises orthoxylene, metaxylene, and ethylbenzene. A SMB system using toluene as a desorbent ("light" SMB unit) only needs the extract and raffinate towers, since the extract tower separates out both the toluene in the desorbent stream as well as trace toluene in the xylene feed. Where two raffinates are withdrawn from a SMB system as described in US 2015/0266794A, two raffinate towers will be required for recovery of desorbent. This increases the capital investment, especially for a retrofit applications of a SMB system.

Thus, there is a need for a process for producing paraxylene that achieves a high paraxylene separation efficiency, avoids the undesired accumulation of ethylbenzene in the xylene loop, and reduces the need for distillation towers, thereby lowering the costs, while avoiding degradation and loss of the desorbent.

SUMMARY OF THE INVENTION

The present invention is directed to a process for producing paraxylene in which two raffinate streams are withdrawn from a SMB paraxylene recovery process. The raffinate streams are withdrawn such that one raffinate stream, a desorbent-rich raffinate stream, contains the majority of desorbent and a small amount of ethylbenzene, and the other raffinate stream, a desorbent-lean raffinate stream, contains a minor amount of desorbent and a substantial amount of ethylbenzene. The desorbent may be removed from the desorbent-rich raffinate stream, and the paraxylene-depleted $C_8$ aromatics portion remaining, comprising metaxylene, orthoxylene, and a small amount of ethylbenzene, is subjected to liquid phase isomerization to obtain an effluent comprising an equilibrium xylenes mixture having a greater concentration of paraxylene than the desorbent-rich raffinate stream, which can be recycled to the SMB process. The desorbent-lean raffinate stream can be directly fed, without an intervening separation of desorbent, to a refinery process or a vapor phase isomerization unit to convert the ethylbenzene therein and produce an equilibrium xylenes mixture having a greater concentration of paraxylene than the desorbent-lean raffinate stream, which can be recycled to the SMB process. Omitting the separation of desorbent prior to the refinery process or vapor phase isomerization saves energy and improves the efficiency of the process, and because the amount of desorbent in the desorbent-lean raffinate stream is minimal, the degradation of desorbent by cracking is minimized, resulting in minimal desorbent loss.

In one aspect, the present invention provides a process for producing paraxylene in which a first mixture comprising ≥5.0 wt % of aromatic $C_8$ isomers, said $C_8$ isomers comprising paraxylene, ethylbenzene, metaxylene, and orthoxylene is provided to a simulated moving bed apparatus comprising use of a desorbent. The simulated moving bed apparatus produces (i) a paraxylene-rich extract, (ii) a desorbent-rich raffinate, and (iii) a desorbent-lean raffinate. The paraxylene-rich extract comprises ≥50.0 wt % of the paraxylene in the first mixture. The desorbent-rich raffinate comprises metaxylene, orthoxylene, ethylbenzene, and ≥75 wt % of the desorbent withdrawn in the desorbent-rich raffinate and a desorbent-lean raffinate. The desorbent-lean raffinate comprises metaxylene, orthoxylene, ethylbenzene, and ≤25 wt % of the desorbent withdrawn in the desorbent-rich raffinate and the desorbent-lean raffinate.

At least a portion of the desorbent-lean raffinate is passed, without an intervening separation, to (i) a vapor phase isomerization reaction to produce a first reaction effluent comprising paraxylene in a greater concentration than the desorbent-lean raffinate, (ii) a refinery process, or both. At least a portion of the desorbent-rich raffinate is passed to a liquid phase isomerization reaction to produce a second reaction effluent comprising paraxylene in a greater concentration than the desorbent-rich raffinate, and at least a portion of the second effluent is recycled to the simulated moving bed apparatus.

In another aspect, the present invention provides a process for producing paraxylene in which a first mixture comprising ≥5.0 wt % of aromatic $C_8$ isomers, said $C_8$ isomers comprising paraxylene, metaxylene, orthoxylene, and ethylbenzene, is provided to a first separation stage to produce a $C_8$ aromatics stream and a $C_{9+}$ hydrocarbon stream. The $C_8$ aromatics stream is separated in a second separation stage comprising a simulated moving bed apparatus comprising use of a desorbent to produce (i) a paraxylene-rich extract, (ii) a desorbent-rich raffinate, and (iii) a desorbent-lean raffinate. The paraxylene-rich extract comprises ≥50.0 wt % of the paraxylene in the first mixture. The desorbent-rich raffinate comprises metaxylene, orthoxylene, ethylbenzene, and ≥75 wt % of the desorbent withdrawn in the desorbent-rich raffinate and a desorbent-lean raffinate. The desorbent-lean raffinate comprises metaxylene, orthoxylene, ethylbenzene, and ≤25 wt % of the desorbent withdrawn in the desorbent-rich raffinate and the desorbent-lean raffinate.

At least a portion of the desorbent-lean raffinate is passed, without an intervening separation step, to a vapor phase isomerization reaction to produce a first reaction effluent comprising paraxylene in a greater concentration than the desorbent-lean raffinate. At least a portion of the desorbent-rich raffinate is passed to liquid phase isomerization reaction to produce a second reaction effluent comprising paraxylene in a greater concentration than the desorbent-rich raffinate. At least a portion of the first reaction effluent and the second reaction effluent is then recycled to the first separation stage or the second separation stage.

DETAILED DESCRIPTION OF THE INVENTION

The present invention is directed to a process for producing paraxylene in which two raffinate streams are withdrawn from a SMB paraxylene recovery process. The raffinate streams are withdrawn such that one raffinate stream, a desorbent-rich raffinate stream, contains the majority of desorbent and a small amount of ethylbenzene, and the other raffinate stream, a desorbent-lean raffinate stream, contains a minor amount of desorbent and a substantial amount of ethylbenzene.

The desorbent-rich raffinate stream is sent to a raffinate tower to remove the desorbent, and the paraxylene-depleted $C_8$ aromatics portion remaining, comprising metaxylene, orthoxylene, and a small amount of ethylbenzene, is subjected to liquid phase isomerization to obtain an effluent comprising an equilibrium xylenes mixture having a greater concentration of paraxylene than the desorbent-rich raffinate stream, which can be recycled to the SMB process.

The desorbent-lean raffinate stream can be directly fed to a vapor phase isomerization unit to convert the ethylbenzene therein and produce an equilibrium xylenes mixture having a greater concentration of paraxylene than the desorbent-lean raffinate stream, which can be recycled to the SMB process. The desorbent-lean raffinate stream may be sent to vapor phase isomerization without removal of the desorbent upstream of the isomerization unit, eliminating the need for a raffinate distillation tower upstream of the vapor phase isomerization unit. Because the amount of desorbent in the desorbent-lean raffinate stream is minimal, the degradation of desorbent by cracking is minimized, resulting in minimal desorbent loss. Thus, the advantages of eliminating a tower may outweigh the disadvantage of losing desorbent during isomerization. When toluene or other desorbents less prone to cracking during isomerization than PDEB are used, the degradation of desorbent can be even avoided, resulting in no loss of desorbent. Alternatively, the desorbent-lean raffinate can be directly sent to another refinery process, such as into a motor gas pool, without a need of being further processed, eliminating subsequent separations or treatments and improving the efficiency of the process.

Figure 1:
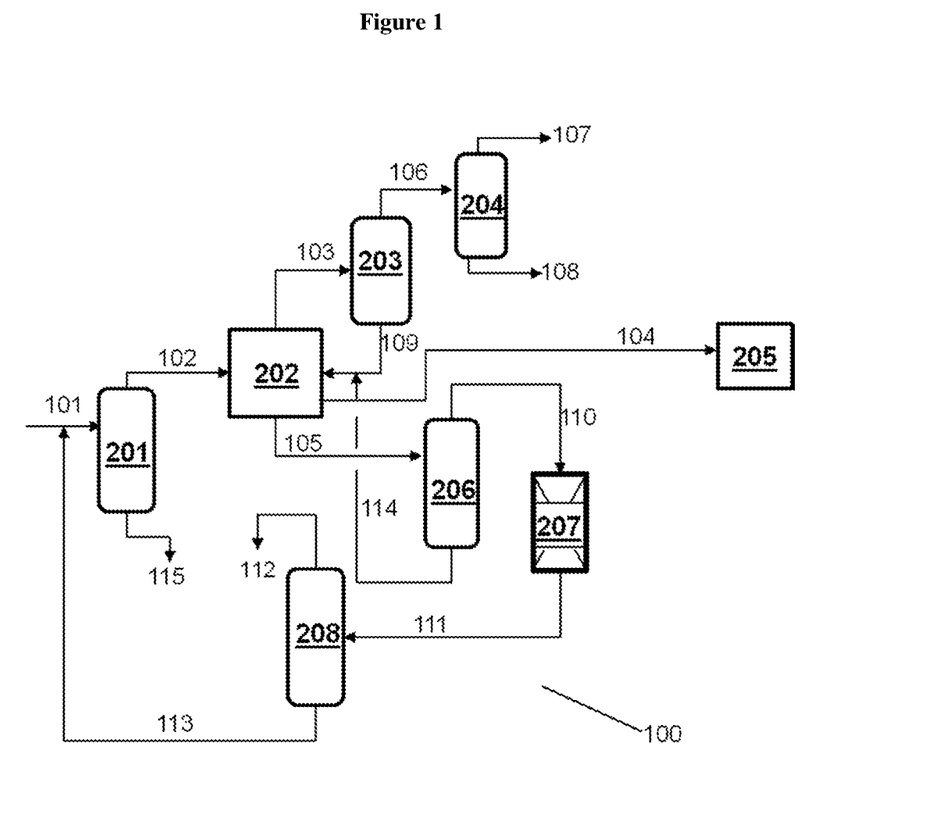
FIG. 1 illustrates a paraxylene separation process according to one aspect of the invention.
Figure 2:
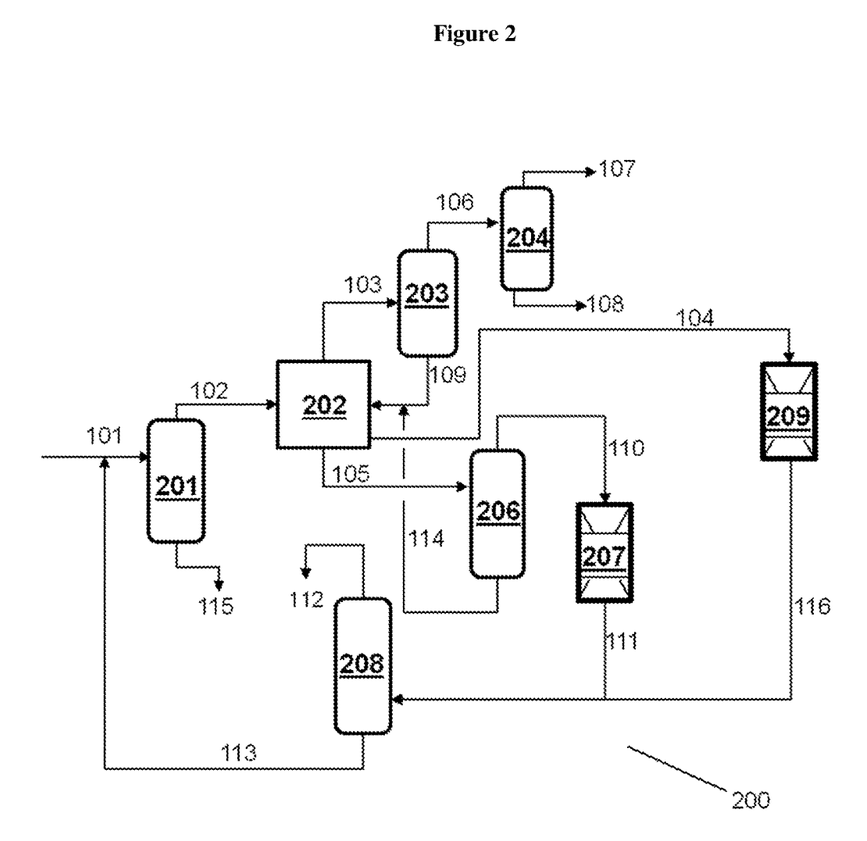
FIG. 2 illustrates a paraxylene separation process according to another aspect of the invention.

The following description relates to aspects of the invention which do not require removal of desorbent from a desorbent-lean raffinate upstream of isomerization. The invention is not limited to these aspects, and is not meant to foreclose other aspects within the broader scope of the invention, such as those which include non-aromatics separation. FIG. 1 schematically illustrates a process 100 which features certain aspects of the invention. FIG. 2 schematically illustrates a process 200 which features certain other aspects of the invention. Similar elements are indicated with identical reference numbers in FIGS. 1 and 2.

A first mixture 101 is passed to a first separation stage 201 to separate a $C_8$ aromatics stream 102 from a $C_{9+}$ hydrocarbon stream 115. The first separation stage 201 may be any suitable separation means, e.g., distillation tower, stabilization tower, flash drum, etc. The $C_8$ aromatics stream 102 is then passed to a second separation stage 202 to recover a paraxylene-rich extract 103, a desorbent-lean raffinate 104, and a desorbent-rich raffinate 105. Alternatively, the first separation stage 201 may be omitted and the first mixture 101 provided directly to the second separation stage 202.

The first mixture typically comprises ≥5.0 wt % of aromatic $C_8$ isomers, said aromatic $C_8$ isomers comprising paraxylene, metaxylene, orthoxylene, and ethylbenzene. Generally, the content of aromatic $C_8$ isomers in the first mixture may range from 5.0 to 100.0 wt %. In particular aspects, the first mixture comprises ≥50.0 wt %, or ≥60.0 wt %, or ≥75.0 wt %, of a mixture of paraxylene, ethylbenzene, metaxylene, and orthoxylene, based on the weight of the first mixture.

The separation stage 202 is preferably a simulated moving bed absorptive separation unit having solvent (sometimes referred to as "desorbent") circulating therethrough via one or more pumps and associated lines (not shown). In particular aspects the second separation stage 202 is a chromatographic separation stage. Circulating solvent should be selected to separate under the separation conditions, e.g., solvent flow, temperature, etc., the components of the first mixture as desired. Typical desorbent has a different boiling point than the $C_8$ aromatics and is easily separated from $C_8$ aromatics in a distillation process. Examples of desorbent include paradiethylbenzene (PDEB), toluene, tetralin, or a mixture thereof. For optimum results with the present invention, the desorbent is preferably toluene, tetralin, or their mixture. Exemplary separation processes are described in U.S. Pat. No. 7,915,471, incorporated herein by reference in its entirety.

The process 100 or 200 may include separating at least a portion of any non-aromatic hydrocarbon molecules from the first mixture in first separation stage 201 or the second separation stage 202. Separation stage 201 or 202 may remove from 5.0 to 100 wt % of any non-aromatic hydrocarbons, based on the amount of such hydrocarbons in the first mixture. In particular aspects, the separation stage 201 or 202 removes ≥50.0 wt %, preferably ≥75.0 wt %, or more preferably ≥90.0 wt % of the non-aromatic hydrocarbons. Certain non-aromatic hydrocarbon molecules, e.g., $C_9$ non-aromatic molecules, have approximately the same volatility as paraxylene. It is conventional to ameliorate problems associated with non-aromatics separation from the xylene loop by cracking at least a portion of the non-aromatics during xylene isomerization. However, this approach lessens xylene loop efficiency (as a result of, e.g., bottlenecking of the isomerization stage), and leads to an increase in separation complexity as a result of the need to remove the cracked products. It has been found that this difficulty can be overcome by removing at least a portion of the non-aromatics upstream of the isomerization, e.g., by removing non-aromatics from the mixtures in separation stages 201 or 202. Advantageously, non-aromatics separation can be carried out in the same simulated moving bed adsorption chromatographic separation using the same desorbent. The chromatographic separation can be carried out using conventional methods, such as those described in U.S. Pat. No. 3,662,020, which is incorporated by reference herein in its entirety. One or more conventional desorbents can be used, e.g., toluene. Conventional configurations can be utilized for the simulated moving bed adsorption chromatographic separation of the second separation stage, e.g., stacked-bed mode and/or multiple bed mode. Suitable configurations are disclosed in U.S. Pat. No. 2,985,589 and U.S. Pat. No. 3,310,486, which are incorporated by reference herein in their entirety. Since at least part of the first mixture's non-aromatics can be separated and conducted away, the process optionally includes subjecting to isomerization conditions ≤90.0 wt % of the first mixture's non-aromatics, e.g., ≤50.0 wt %, such as ≤25.0 wt %. In certain aspects, the process includes subjecting ≤10.0 wt % of the first mixture's non-aromatics to isomerization conditions, e.g., ≤5.0 wt %, such as ≤1.0 wt %.

Separation stage 202 should be operated such that paraxylene-rich extract 103 comprises ≥50.0 wt % of the paraxylene in the first mixture. Generally, the content of paraxylene in paraxylene-rich extract 103 may range from 50.0 to 100.0 wt % of the paraxylene in the first mixture. In particular aspects, paraxylene-rich extract 103 preferably comprises ≥75.0 wt %, more preferably ≥85.0 wt %, and most preferably ≥95.0 wt %, of the paraxylene in the first mixture.

The paraxylene-rich extract 103 separated from the second separation stage 202 can be provided to a third separation stage 203 for separation of desorbent 109 to produce a paraxylene extract 106, and then the paraxylene extract 106 can be provided to a fourth separation stage 204, in which other by-products 107, e.g., benzene and water, are further removed and a pure paraxylene product 108 is recovered. The desorbent 109 removed from the third separation stage 203 can be recycled to the second separation stage 202. In the third separation stage 203, ≥90 wt %, preferably ≥95 wt %, more preferably ≥99 wt %, and ideally ≥99.9 wt % of desorbent contained in the paraxylene-rich extract 103 is removed.

The process 100 or 200 produces two raffinates—a desorbent-lean raffinate 104 and desorbent-rich raffinate 105. The desorbent-lean raffinate 104 preferably comprises ≤25.0 wt %, more preferably ≤10 wt %, and most preferably ≤5.0 wt %, of the desorbent withdrawn in both the desorbent-rich and desorbent-lean raffinates. Accordingly, the desorbent-rich raffinate 105 preferably comprises ≥75 wt %, more preferably ≥90 wt %, and most preferably ≥95.0 wt %, of the desorbent withdrawn in both the desorbent-rich and desorbent-lean raffinates.

In some aspects, the raffinate streams are fractioned such that more raffinate is withdrawn as the desorbent-rich raffinate 105. For example, the desorbent-rich raffinate 105 may be ≥60 wt %, or ≥70 wt %, or ≥80 wt %, of the total raffinate withdrawn.

The desorbent-lean raffinate 104 and the desorbent-rich raffinate 105 may collectively comprise ≥10.0 wt %, preferably ≥30.0 wt %, more preferably ≥50.0 wt %, most preferably ≥75.0 wt %, and ideally ≥90.0 wt %, of the ethylbenzene in the first mixture.

The desorbent-lean raffinate 104 may comprise ≥30.0 wt %, preferably ≥45.0 wt %, more preferably ≥60.0 wt %, and most preferably ≥75.0 wt %, of the ethylbenzene in the first mixture. The desorbent-lean raffinate 104 typically comprises ≥5.0 wt % of ethylbenzene based on the weight of desorbent-lean raffinate. The lower limit on content of ethylbenzene in the desorbent-lean raffinate can be 5.0 wt %, or 7.5 wt %, or 10.0 wt % by weight of the desorbent-lean raffinate. The upper limit on content of ethylbenzene in the desorbent-lean raffinate can be 50.0 wt %, or 30.0 wt %, or 15.0 wt % by weight of the desorbent-lean raffinate. In some aspects, the ethylbenzene concentration by weight in the desorbent-lean raffinate can be higher than the ethylbenzene concentration by weight in desorbent-rich raffinate.

The desorbent-rich raffinate 105 may comprise ≤70 wt %, preferably ≤50 wt %, more preferably ≤30 wt %, and most preferably ≤10 wt %, of the ethylbenzene in the first mixture. The desorbent-rich raffinate 105 typically comprises ≤30 wt % of ethylbenzene based on the weight of desorbent-rich raffinate. The lower limit on content of ethylbenzene in the desorbent-rich raffinate can be 0.5 wt %, or 1.0 wt %, or 2.5 wt % by weight of the desorbent-rich raffinate. The upper limit on content of ethylbenzene in the desorbent-rich raffinate can be 25 wt %, or 15 wt %, or 5 wt % by weight of the desorbent-rich raffinate.

The desorbent-lean raffinate 104 may comprise at least a portion of the first mixture's metaxylene and orthoxylene, e.g., ≤50.0 wt %, or 40.0 wt %, or 30.0 wt % of the first mixture's metaxylene and ≤50.0 wt %, or 40.0 wt %, or 30.0 wt % of the first mixture's orthoxylene. Accordingly, the desorbent-rich raffinate 105 may comprise at least a portion of the first mixture's metaxylene and orthoxylene, e.g., ≥50.0 wt %, or 60.0 wt %, or 70.0 wt %, or 80.0 wt % of the first mixture's metaxylene and ≥50.0 wt %, or 60.0 wt %, or 70.0 wt %, or 80.0 wt % of the first mixture's orthoxylene.

The positions of withdrawing the desorbent-rich raffinate and the desorbent-lean raffinate are not particularly limited so long as the desorbent-lean raffinate and the desorbent-rich raffinate according to the present invention can be obtained. For example, the positions of withdrawing the desorbent-rich and desorbent-lean raffinates can be distanced by 2, 3, 4 or 5 adsorption beds. In some aspects, the desorbent-lean raffinate is positioned upstream of the desorbent-rich raffinate along the direction of the circulating solvent flows.

At least a portion of the desorbent-lean raffinate 104 can be sent, without an intervening separation, to a refinery process 205, for example, a motor gas pool, as shown in FIG. 1. By doing such, a further separation or treatment to the desorbent-lean raffinate 104 is eliminated, which accordingly lowers the cost of the process and improves the economical effect. In another embodiment (not shown in FIGS. 1 and 2), at least a portion of the desorbent-lean raffinate 104 can be recycled back to the second separation stage 202 to flush the lines in and out of the simulated moving bed apparatus with at least a portion of the recovered desorbent-lean raffinate before the lines are switched for transferring feed, extract, desorbent, or raffinates.

In another aspect, shown in FIG. 2, the desorbent-lean raffinate 104 is provided, without an intervening separation, to reactor 209, where the desorbent-lean raffinate is isomerized under vapor phase conditions to produce a first reaction effluent 116 comprising aromatic $C_8$ isomers. The first reaction effluent 116 comprises a greater concentration of paraxylene than the desorbent-lean raffinate 104 and is recycled back to the first separation stage 201 or second separation stage 202. The vapor phase isomerization reaction may employ any suitable catalyst and process conditions known in the art effective to convert ethylbenzene. In one embodiment, the vapor phase isomerization reaction deethylates the ethylbenzene and isomerizes the metaxylene and orthoxylene to produce an equilibrium mixture of xylenes. In another embodiment, the vapor phase isomerization reaction isomerizes the ethylbenzene along with the metaxylene and orthoxylene to produce an equilibrium mixture of xylenes. U.S. Ser. No. 14/969,298 describes the different catalysts and process conditions that may be used for the vapor phase isomerization reaction. In the vapor phase isomerization reaction in reactor 209, generally greater than 50.0 wt %, preferably ≥60 wt %, more preferably ≥80.0 wt %, most preferably ≥90.0 wt %, and ideally ≥95.0 wt % of the desorbent-lean raffinate 104 in reactor 209 is in the vapor phase during the reacting, the weight percent being based on the weight of the desorbent-lean raffinate.

The desorbent-rich raffinate 105 is provided to a fifth separation stage 206 to separate and remove desorbent from the desorbent-rich raffinate to obtain a raffinate 110. The resulting raffinate 110 is then provided to a reactor 207, where the raffinate 110 is isomerized under liquid phase conditions to produce a second reaction effluent 111 comprising aromatic $C_8$ isomers. The second reaction effluent 111 comprises a greater concentration of paraxylene than the desorbent-rich raffinate 105 and is recycled back to the first separation stage 201 or second separation stage 202. If the second reaction effluent 111 is sufficiently devoid of $C_{9+}$ aromatics, the second reaction effluent 111 may be recycled directly to the second separation stage 202. The liquid phase isomerization reaction may employ any catalyst and process conditions known in the art effective to isomerize metaxylene and orthoxylene to produce an equilibrium mixture of xylenes. U.S. Ser. No. 14/969,298 describes a preferred catalyst and process conditions for the liquid phase isomerization reaction. While the isomerization reaction in reactor 207 is conducted in the liquid phase, some of the raffinate 110 may be in the vapor phase. Thus, in particular aspects, ≤10.0 wt %, preferably ≤7.5 wt %, more preferably ≤5.0 wt %, most preferably ≤2.5 wt %, and ideally ≤1.0 wt %, of the raffinate 110 in reactor 207 is in the vapor phase during the isomerization reaction, the weight percent based on the weight of the raffinate 110.

The first reaction effluent 116 and second reaction effluent 111 generally comprise products formed in reactors 209 and 207, but can also include unreacted raffinates. The first reaction effluent 116 and the second reaction effluent 111 may have similar compositions. For example, the first and second reaction effluents can comprise $C_1$-$C_7$ compounds, $C_8$ aromatic isomers, and $C_{9+}$ aromatics.

Optionally, the first reaction effluent 116 and the second reaction effluent 111 can be provided to a sixth separation stage 208, where at least a portion of one or more $C_1$-$C_7$ compounds in the first and second reaction effluents 111, 116 are separated via an overhead stream 112. Particular aspects of the process include conducting the separated one or more $C_1$-$C_7$ compounds away from the process. Heavier compounds, including aromatic $C_8$ isomers and $C_{9+}$ hydrocarbons, exit the sixth separation stage 208 as $C_{8+}$ hydrocarbon stream 113. Separation stage 208 may be any separation means suitable for separating $C_1$-$C_7$ compounds from $C_{8+}$ hydrocarbons. In particular aspects, separation stage 208 is a stabilization column or distillation column. Typically, the $C_1$-$C_7$ compounds are separated in separation stage 208 before the reaction effluent(s) is recycled for combining with the first mixture 101, as shown in FIGS. 1 and 2. In other words, the $C_1$-$C_7$ compounds are separated and at least a portion of the $C_{8+}$ hydrocarbons 113 from the separation stage 208 are recycled to the first separation stage 201 or the second separation stage 202. Any desirable amount of the $C_{8+}$ hydrocarbon stream 113 exiting separation stage 208 may be recycled. Typically, ≥50.0 wt %, preferably ≥75.0 wt %, more preferably ≥90.0 wt %, and most preferably 100.0 wt % of the $C_{8+}$ hydrocarbon stream 113, based on the total amount of $C_{8+}$ hydrocarbons exiting separation stage 208, are recycled. In particular aspects, the $C_{8+}$ hydrocarbon stream 113 comprises ≥50.0 wt % $C_{8+}$ aromatic hydrocarbons (e.g., ethylbenzene, orthoxylene, metaxylene, paraxylene). In particular aspects, the aromatic $C_{8+}$ hydrocarbons comprise ≥50.0 wt % paraxylene.

EXAMPLES

The following example describes the advantages of the present invention. A detailed mathematical model is developed to simulate a general SMB operation for paraxylene separation from the mixed xylenes. This model is then used to demonstrate the concept of fractionating multiple raffinate streams with drastically different compositions of EB and the desorbent.

Model Description:

An SMB unit that consists of 24 beds was employed. A feed comprising a mixture of $C_8$ aromatics (paraxylene (PX), orthoxylene (OX), metaxylene (MX), and ethylbenzene (EB)) and desorbent (para-diethylbenzene (PDEB)) was fed to the SMB unit. A paraxylene-rich extract, a desorbent-rich raffinate, and a desorbent-lean raffinate were withdrawn from the unit.

The following assumptions are made referring to "Modeling and Simulation of a Simulated Moving Bed for the Separation of Paraxylene", *Industrial & Engineering Chemistry Research*, 41 (2002) 3454-61, by M. Minceva and A. E. Rodrigues et al.: the separation is conducted under isothermal and isobaric conditions; the velocity of each stream is constant; a solid phase concentration is homogeneous throughout adsorbent particles and a mass transfer between the liquid and adsorbent phases is described by the Linear Driving Force (LDF) model.

Based on the above assumptions, mass balance equations was written as:

$$\frac{\partial C_{ik}(z,t)}{\partial t} = \mathcal{D}_{Lk}(t)\frac{\partial^2 C_{ik}(z,t)}{\partial z^2} - v_k^*(t)\frac{\partial C_{ik}(z,t)}{\partial z} - \frac{(1-\varepsilon)}{\varepsilon}\frac{\partial q_{ik}(z,t)}{\partial t}$$

where i is the index for components (i=PX, MX, OX, EB, PDEB); k is the index for columns (k=1 ... $N_{bed}$, where $N_{bed}$ is the total number of beds); C is the bulk liquid concentration $$\left(\text{unit }\frac{kg}{m^3}\right);$$

q is the adsorbate concentration $$\left(\text{unit }\frac{kg}{m^3}\right);$$

$\varepsilon$ is the overall porosity; D is the axial dispersion coefficient; and $v^*_k$ is the interstitial velocity in columns.

This mass balance equation described the change of bulk liquid concentration at a specific position inside of a column (first term) with respect to dispersion (second term), convection (third term), and adsorption/desorption process (fourth term).

The LDF model is written as:

$$\frac{\partial q_{ik}(z,t)}{\partial t} = k(q_{ik}^*(z-t) - q_{ik}(z,t))$$

where q* is the adsorbate concentration in equilibrium with the liquid phase $$\left(\text{unit}\frac{kg}{m^3}\right).$$

The LDF model describes the mass flux into the solid phase. The adsorbate concentration in equilibrium with the liquid phase can be obtained from an adsorption isotherm.

At the node between columns, the mass balance is calculated by subtracting outlet flow rates and adding inlet flow rates:

$$F_{k+1} = F_k + F_{Feed,k} + F_{desorbent,k} - F_{raffinate,k} - F_{extract,k}$$

For columns that are not connected to inlet or outlet streams, $F_{Feed,k}$ or $F_{desorbent,k}$ or $F_{raffinate,k}$ or $F_{extract,k}$ is zero.

The dynamics of the SMB system reach a cyclic steady state (CSS) where the concentration profiles in a bed at the beginning of the step are exactly identical to the concentration profiles in the next bed at the end of the step. The CSS constraints are given as:

$$C_{k+1}(z, t_{end}) = C_k(z, t_0)$$

where $t_{end}$ is the time at the end of a step, and $t_0$ is the beginning of a step. Here, step-symmetric operation is assumed, i.e., each step is exactly identical except the inlet and outlet locations are different.

Model Optimization:

The optimization problem was formulated as follows:

Objective function: minimize $F_{desorbent}$,

Decision variables: $F_1$, $F_2$, $F_3$, $F_4$, $t_{st}$, where $F_j$'s are zone flow rates, j equals to 1, 2, 3, 4, and $t_{st}$ is the step time;

Main Constraint: Extract purity (PX)≥98.0%,

Extract recovery (PX)≥97.0%.

The model was discretized into a set of algebraic differential equations by applying the center finite difference method (CFDM) to the spatial domain and orthogonal collocation finite element method (OCFEM) to the temporal domain respectively. The discretized problem was solved by an interior-point optimization algorithm (IPOPT) as described by A. Wachter and L. T. Biegler, On the Implementation of a Primal-Dual Interior Point Filter Line Search Algorithm for Large-Scale Nonlinear Programming, Mathematical Programming 106(1), pp. 25-57, 2006.

In addition to the optimization stated above, an additional constraint was imposed to ensure 50% of EB introduced into the SMB system is recovered in the desorbent-lean raffinate stream. The optimization results are shown in Tables 1 and 2. Table 1 shows the optimized mass flow rates of each component in the product outlets. The amount of desorbent was unevenly split between the two raffinate streams. The desorbent-rich raffinate stream, Raffinate 1 (R1), contains 79.7 wt % of PDEB, based on the total amount of PDEB in both raffinates, and the desorbent-lean raffinate stream, Raffinate 2 (R2), contained 20.3 wt % of PDEB, based on the total amount of PDEB in both raffinates. Because the amount of PDEB in the desorbent-lean raffinate is minimal, the requirement of having a second distillation tower for the extraction of desorbent can be eliminated, and Raffinate 2 can be directly fed to a reactor for vapor phase isomerization or used in a refinery operation.

TABLE 1 mass flow rates (kg/min) in both inlet and outlet streams at the cyclic steady state

| | OX | PX | MX | EB | PDEB |
|---|---|---|---|---|---|
| Feed | 336.6 | 625.5 | 1317.2 | 371 | 0 |
| Desorbent | 0 | 0 | 0 | 0 | 3398.7 |
| Raffinate 1 (desorbent-rich) | 189.5 | 0.07 | 708.2 | 173.6 | 1006.7 |
| Raffinate 2 (desorbent-lean) | 147.4 | 18.7 | 610.3 | 185.6 | 256.7 |
| Extract | 0 | 606.7 | 0.15 | 12.23 | 2132.9 |

Table 2 shows the purity and recovery obtained in all the product outlets. The PX purity and recovery obtained in the extract were 98.00% and 97.00%, respectively, which meets the specifications for industrial uses. In addition, the Raffinate 2 recovered 50% of the EB introduced into the SMB system, thus preventing EB from building up in the xylene loop.

TABLE 1

Purity and recovery of various components in the product outlets

|  | OX | PX | MX | EB |
|---|---|---|---|---|
| Raffinate 1 purity | 17.69% | 0.01% | 66.10% | 16.20% |
| Raffinate 1 recovery | 56.31% | 0.01% | 53.77% | 46.78% |
| Raffinate 2 purity | 15.33% | 1.94% | 63.44% | 19.29% |
| Raffinate 2 recovery | 43.81% | 2.99% | 46.33% | 50.03% |
| Extract purity | 0.00% | 98.00% | 0.02% | 1.98% |
| Extract recovery | 0.00% | 97.00% | 0.01% | 3.30% |

Figure 3:
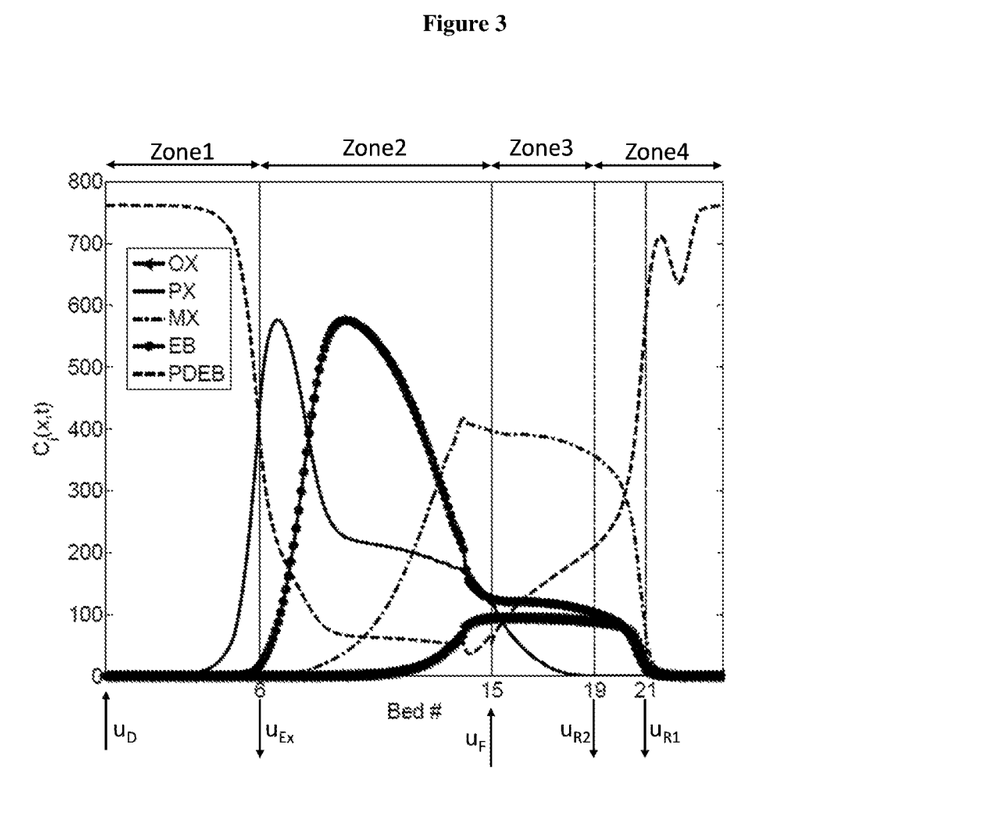
FIG. 3 illustrates an example of a concentration profile of $C_8$ aromatic hydrocarbons and desorbent in a simulated moving bed separation system.

FIG. 3 shows the optimized internal concentration profiles inside the SMB system. The entire figure is divided into four zones based on the inlet and outlet streams. The symbols $u_F$, $u_D$, $u_{R1}$, $u_{R2}$ and $u_{Ex}$ refer to the feed, desorbent, first raffinate, second raffinate and extract locations, respectively. The R1 and R2 streams are distanced by 3 beds. The two raffinate streams were fractionated in such a way that the paraxylene recovery in the extract stream was not sacrificed, but R1 contained substantially more desorbent than R2. Moreover, the R2 stream may be withdrawn at a location to include a majority of the ethylbenzene and the R1 stream may be withdrawn at a location to include a minor amount of the ethylbenzene, enabling the use of both liquid and vapor phase isomerization technologies for downstream processing. Hence, the need for an additional raffinate tower for the second raffinate, R2, can be avoided.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements.

What is claimed is:

1. A process for producing paraxylene, the process comprising:
   (a) providing a first mixture comprising ≥5.0 wt % of aromatic $C_8$ isomers, said $C_8$ isomers comprising paraxylene, metaxylene, orthoxylene, and ethylbenzene;
   (b) separating the first mixture in a simulated moving bed apparatus comprising use of a desorbent to produce a paraxylene-rich extract, a desorbent-rich raffinate, and a desorbent-lean raffinate,
   wherein the paraxylene-rich extract comprises ≥50.0 wt % of the paraxylene in the first mixture,
   wherein the desorbent-rich raffinate comprises metaxylene, orthoxylene, ethylbenzene, and ≥75 wt % of the desorbent withdrawn in the desorbent-rich raffinate and the desorbent-lean raffinate, and
   wherein the desorbent-lean raffinate comprises metaxylene, orthoxylene, ethylbenzene, and ≤25 wt % of the desorbent withdrawn in the desorbent-rich raffinate and the desorbent-lean raffinate;
   (c) passing, without an intervening separation step, at least a portion of the desorbent-lean raffinate to (i) a vapor phase isomerization reaction to produce a first reaction effluent having a higher paraxylene concentration than the desorbent-lean raffinate, (ii) a refinery process, or both;
   (d) passing at least a portion of the desorbent-rich raffinate to a liquid phase isomerization reaction to produce a second reaction effluent having a higher paraxylene concentration than the desorbent-rich raffinate; and
   (e) recycling at least a portion of the second reaction effluent from step (d) to the separating of step (b).

2. The process of claim 1, wherein step (c) comprises passing the desorbent-lean raffinate to a vapor phase isomerization reaction.

3. The process of claim 2 further comprising;
   (f) recycling at least a portion of the first reaction effluent from step (c) to the separating of step (b).

4. The process of claim 1, wherein the vapor phase isomerization reaction in step (c) comprises contacting the desorbent-lean raffinate with a catalyst and process conditions effective to deethylate the ethylbenzene and isomerize the metaxylene and orthoxylene.

5. The process of claim 1, wherein the vapor phase isomerization reaction in step (c) comprises contacting the desorbent-lean raffinate with a catalyst and process conditions effective to isomerize the ethylbenzene, metaxylene, and orthoxylene.

6. The process of claim 1, further comprising before step (e):
   (d') separating from the second reaction effluent of step (d) (i) at least a portion of $C_1$-$C_7$ compounds, (ii) at least a portion of orthoxylene and/or $C_{9+}$ aromatics, or both.

7. The process of claim 3, further comprising before step (f):
   (c') separating from the first reaction effluent of step (c) (i) at least a portion of $C_1$-$C_7$ compounds, (ii) at least a portion of orthoxylene and/or $C_{9+}$ aromatics, or both.

8. The process of claim 1, wherein the desorbent-lean raffinate comprises ≤10.0 wt % of the desorbent withdrawn in the desorbent-rich raffinate and a desorbent-lean raffinate.

9. The process of claim 8, wherein the desorbent-lean raffinate comprises ≥30.0 wt % of the ethylbenzene in the first mixture.

10. The process of claim 1, wherein the desorbent-rich raffinate comprises ≤40 wt % of the ethylbenzene in the first mixture.

11. The process of claim 1, wherein the paraxylene-rich extract comprises ≥90.0 wt % of the paraxylene in the first mixture.

12. The process of claim 1, wherein the desorbent-rich raffinate and the desorbent-lean raffinate comprise ≥90.0 wt % of the ethylbenzene in the first mixture.

13. The process of claim 1, wherein ≥50.0 wt % of the second reaction effluent from step (d) is recycled in step (f).

14. The process of claim 3, wherein ≥50.0 wt % of the first reaction effluent from step (c) is recycled in step (e).

15. The process of claim 1, wherein the first mixture comprises ≥50.0 wt % of a mixture of paraxylene, ethylbenzene, metaxylene, and orthoxylene.

16. The process of claim 1, wherein the desorbent comprises at least one of para-diethylbenzene, toluene and tetralin.

17. A process for producing paraxylene, the process comprising:
   (a) providing a first mixture comprising ≥5.0 wt % of aromatic $C_8$ isomers, said $C_8$ isomers comprising paraxylene, metaxylene, orthoxylene, and ethylbenzene, to a first separation stage to produce a $C_8$ aromatics stream and a $C_{9+}$ hydrocarbon stream;

(b) separating the $C_8$ aromatics stream in a second separation stage comprising a simulated moving bed apparatus comprising use of a desorbent to produce a paraxylene-rich extract, a desorbent-rich raffinate, and a desorbent-lean raffinate, wherein the paraxylene-rich extract comprises ≥50.0 wt % of the paraxylene in the first mixture, wherein the desorbent-rich raffinate comprises metaxylene, orthoxylene, ethylbenzene, and ≥75 wt % of the desorbent withdrawn in the desorbent-rich raffinate and the desorbent-lean raffinate, and wherein the desorbent-lean raffinate comprises metaxylene, orthoxylene, ethylbenzene, and ≤25 wt % of the desorbent withdrawn in the desorbent-rich raffinate and the desorbent-lean raffinate;

(c) passing, without an intervening separation step, at least a portion of the desorbent-lean raffinate to a vapor phase isomerization reaction to produce a first reaction effluent having a higher paraxylene concentration than the desorbent-lean raffinate;

(d) passing at least a portion of the desorbent-rich raffinate to liquid phase isomerization reaction to produce a second reaction effluent having a higher paraxylene concentration than the desorbent-rich raffinate; and (e) recycling at least a portion of the first reaction effluent from step (c) and the second reaction effluent from step (d) to the first separation stage of step (a) or the second separation stage of step (b).

18. The process of claim 17 further comprising:

(f) passing the paraxylene-rich extract to a third separation stage to remove the desorbent and produce a paraxylene extract;

(g) recycling the desorbent back to the second separation stage; and (h) passing the paraxylene extract to a fourth separation stage to produce a paraxylene product.

19. The process of claim 17, further comprising prior to step (d):

(d') passing at least a portion of the desorbent-rich raffinate from to a fifth separation stage to remove the desorbent and produce a raffinate, wherein the raffinate is passed to the liquid phase isomerization reaction.

20. The process of claim 17, wherein the first reaction effluent from is recycled to the first separation stage and the second reaction effluent is recycled to the second separation stage.

21. The process of claim 17, wherein the vapor phase isomerization reaction of step (c) comprises contacting the desorbent-lean raffinate with a catalyst and process conditions effective to deethylate the ethylbenzene and isomerize the metaxylene and orthoxylene.

22. The process of claim 17, wherein the vapor phase isomerization reaction of step (c) comprises contacting the desorbent-lean raffinate with a catalyst and process conditions effective to isomerize the ethylbenzene, metaxylene, and orthoxylene.

23. The process of claim 17, wherein the desorbent-lean raffinate comprises ≤10.0 wt % of the desorbent withdrawn in the desorbent-rich raffinate and a desorbent-lean raffinate.

24. The process of claim 23, wherein the desorbent-lean raffinate comprises ≥30.0 wt % of the ethylbenzene in the first mixture, and the desorbent-rich raffinate comprises ≤40 wt % of the ethylbenzene in the first mixture.

25. The process of claim 17, wherein the desorbent-rich raffinate and the desorbent-lean raffinate comprise ≥90.0 wt % of the ethylbenzene in the first mixture.

* * * * *